(12) United States Patent
Liu (10) Patent No.: US 10,800,971 B1
(45) Date of Patent: Oct. 13, 2020

(54) BIOMASS-BASED HIGH-EFFICIENCY FLUORESCENT GRAPHENE QUANTUM DOT AND PREPARATION METHOD THEREOF

(71) Applicants: Guangdong Pharmaceutical University, Guangdong (CN); Guangzhou chengshun Cosmetic Products Co. Ltd., Guangzhou (CN)

(72) Inventor: Yi Liu, Guangdong (CN)

(73) Assignees: Guangdong Pharmaceutical University, Guangdong (CN); Guangzhou chengshun Cosmetic Products Co. Ltd., Guangzhou (CN)

( * ) Notice: Subject to any disclaimer, the term of this patent is extended or adjusted under 35 U.S.C. 154(b) by 0 days.

(21) Appl. No.: 16/551,750

(22) Filed: Aug. 27, 2019

(30) Foreign Application Priority Data

Jun. 21, 2019 (CN) .......................... 2019 1 0544748

(51) Int. Cl.
*C09K 11/65* (2006.01)
*C01B 32/184* (2017.01)
(Continued)

(52) U.S. Cl.
CPC ............ *C09K 11/65* (2013.01); *C01B 32/184* (2017.08); *C01B 32/194* (2017.08); *B82Y 20/00* (2013.01);
(Continued)

(58) Field of Classification Search
CPC ..... C09K 11/65; C01B 32/194; C01B 32/184; B82Y 20/00; C01P 2002/84; C01P 2004/04
See application file for complete search history.

(56) References Cited

FOREIGN PATENT DOCUMENTS

| CN | 105647528 | 6/2016 |
|----|-----------|--------|
| CN | 106829917 | 6/2017 |
| CN | 107353898 | 11/2017 |

OTHER PUBLICATIONS

Safardoust-Hojaghan, et al., Preparation of highly luminescent nitrogen doped graphene quantum dots and their application as a probe for detection of *Staphylococcus aureus* and *E. coli*, Journal of Molecular Liquids 2017; 241: 1114-1119 (Year: 2017).*

(Continued)

*Primary Examiner* — Daniel C. McCracken
(74) *Attorney, Agent, or Firm* — JCIPRNET (57) ABSTRACT

The invention relates to the field of nano materials, in particular to biomass-based high-efficiency fluorescent graphene quantum dot and preparation method thereof. Method for preparing biomass-based high-efficiency fluorescent graphene quantum dots includes hydrothermal reaction of composite carbon source, nitrogen source, polyvalent metal ion and water. The method for preparing a biomass-based high-efficiency fluorescent graphene quantum dot includes the following steps: (1) Mixing the composite carbon source and the nitrogen source, and then adding water, stirring and dissolving to obtain a mixture A; (2) Adding polyvalent metal ions to the mixture A, and after stirring, heating and reacting to obtain a crude product; (3) The crude product is purified by dialysis to obtain a purified product. The biomass-based high-efficiency fluorescent graphene quantum dot of the invention has the characteristics of high fluorescence intensity, high yield, simple preparation method and wide range of application.

8 Claims, 4 Drawing Sheets

(51) Int. Cl.
*C01B 32/194* (2017.01)
*B82Y 20/00* (2011.01)
(52) U.S. Cl.
CPC ...... *C01P 2002/84* (2013.01); *C01P 2004/04* (2013.01)

(56) References Cited

OTHER PUBLICATIONS

Huang, et al., High quantum yield nitrogen-doped carbon dots: green synthesis and application as "off-on" fluorescent sensors for the determination of Fe3+ and adenosine triphosphate in biological samples, Sensors & Actuators: B. Chemical 2018; 276: 82-88 with Supplemental Information. (Year: 2018).*

Li, et al., Nitrogen-Doped Graphene Quantum Dots with Oxygen-Rich Functional Groups, J. Am. Chem. Soc. 2012; 134: 15-18 (Year: 2012).*

Yue Hu et al., "Graphene quantum dots—carbon nanotube hybrid arrays for supercapacitors," Nanotechnology, vol. 24, Apr. 2013, pp. 1-8.

Hui Xia et al., "Facile Synthesis of Hematite Quantum-Dot/Functionalized Graphene-Sheet Composites as Advanced Anode Materials for Asymmetric Supercapacitors," Advanced Functional Materials, vol. 25, Issue 4, Jan. 2015, pp. 627-635.

Xiaoyan Zhou et al., "Microwave irradiation synthesis of Co3O4 quantum dots/graphene composite as anode materials for Li-ion battery," Electrochimica Acta, vol. 143, Oct. 2014, pp. 175-179.

* cited by examiner

BIOMASS-BASED HIGH-EFFICIENCY FLUORESCENT GRAPHENE QUANTUM DOT AND PREPARATION METHOD THEREOF

CROSS-REFERENCE TO RELATED APPLICATION

This application claims the priority benefit of China application serial no. 201910544748.0, filed on Jun. 21, 2019. The entirety of the above-mentioned patent application is hereby incorporated by reference herein and made a part of this specification.

BACKGROUND

Technical Field

The invention relates to the field of nanomaterials, in particular to a biomass-based high-efficiency fluorescent graphene quantum dot and its preparation method.

Description of Related Art

Carbon Quantum Dots (CQDs) are quasi-spherical fluorescent carbon nanomaterial with a monodispersity of 10 nm or less. Following fullerenes, carbon nanotubes and graphene, CQDs are one of the most popular carbon nanomaterials. CQDs are made into fluorescent probes for biological use in vitro and in vivo cell development or as biomarkers, due to their excellent biosafety, environmental friendliness, photoluminescence, hydrophilicity, chemical and light stability, ease of functionalization and electronic properties. Compared with semiconductor quantum dots, carbon quantum dots are widely used in cell imaging, biosensing, drug carriers, ion detection, and optoelectronic devices because of their non-toxicity, good biocompatibility, good stability, good fluorescence adjustability, easy functionalization, and greater resistance to photobleaching. They are particularly concerned by researchers in various fields.

The "carbon sources" used to synthesize carbon quantum dots are generally organic carbon source, such as polysaccharide, pork, apple juice and so on. That also include inorganic carbon source such as graphite and activated carbon. The methods for preparing carbon quantum dots are mainly discharge method, laser method, ultrasonic method, one-step hydrothermal method, chemical oxidation method and microwave method. Hu et al. [Nanotechnology 24(2013):195401] prepared the graphene quantum dot-carbon nanotube composites by electrochemical method. Xia et al. [Adv.Funct.Mater.25(2015):627] prepared the iron oxide quantum dot-graphene sheet composite by thermal decomposition. Zhou et al [Electrochim. Acta. 143 (2014): 175] prepared the cobalt trioxide quantum dots-graphene composites by microwave irradiation. It is found that the one-step hydrothermal method is the best method with advances of simple operation process, short synthesis time and high synthesis efficiency.

The invention patent application of CN 106829917A relates to a carbon quantum dot and its applications as additives in textiles, paper, printed products, cosmetics or fluorescent imaging. Organic polybasic acid and polyamine are used as raw materials to synthesize the crude carbon quantum dots in one step by hydrothermal method, and then purified twice to obtain carbon quantum dots with the 100% quantum yield. Fluorescent materials with the high quantum yield have very high light conversion efficiency, and the carbon quantum dot can withstand photobleaching, so that the carbon quantum dots with the quantum yield of 100% have very wide application prospects. According to the invention, the method for synthesizing the carbon quantum dot is simple, and the carbon quantum dot has high quantum yield and is resistant to photobleaching, and is expected to be applied to the fields of light industrial printing and dyeing and biological medicines. However, its fluorescence intensity is low and its application range is limited.

The invention patent application of CN 105647528A provides a zinc-doped carbon quantum dot and its preparation method, and its application in the field of detection. This is the first time that a high quantum yield of carbon quantum dots is obtained by doping the zinc element with a green, simple one-step hydrothermal method, and the fluorescence quantum yield is as high as 63%. The preparation method specifically includes the steps that the carbon source and the zinc source are dissolved to obtain a precursor solution, which is placed in a hydrothermal reaction kettle for reaction, after the synthesized product is naturally cooled, the solution is separated and dried to obtain a zinc-doped carbon quantum dot with high fluorescence quantum yield. The method requires very few raw materials, has few intermediate products and by-products, and has a fast reaction speed, and the method is economical and environmentally friendly. The light emitting intensity of the zinc-doped carbon quantum dot is high up to $5.8*10^5$, the zinc-doped carbon quantum dot has wide application prospects as a fluorescent probe in biomedical detection, and the zinc-doped carbon quantum dot can be used for trace and quantitative analysis and detection of hydrogen peroxide and glucose. However, its fluorescence quantum yield is low, only 63%, and the lower yield leads to higher costs.

The invention of patent application CN 107353898A discloses a preparation method of boron and nitrogen-doped green fluorescent carbon dots. The preparation method includes the following steps: firstly, preparing a phenylboronic acid solution with deionized water and then mixing the solution with anhydrous ethylenediamine; secondly, introducing nitrogen to react and then cooling to room temperature to obtain a boron and nitrogen-doped carbon quantum dot solution, thirdly, preserving the boron and nitrogen-doped carbon quantum dot solution at low temperature for later use and using carbon quantum dots for selective detection of horse radish peroxidase (HRP). The invention aims at providing the preparation method of the boron and nitrogen-doped green fluorescent carbon dots and the boron and nitrogen-doped green fluorescent carbon dots are prepared by using a hydrothermal method. The obtained carbon quantum dots with spherical structures have the advantages of uniform size and relatively-small average particle size. Agglomeration of the carbon quantum dots can also be avoided due to the action of boric acid functional groups on the surfaces of the carbon quantum dots. The method has the advantages of relatively-simple synthesis process, economy, greenness and environmental friendliness; in addition, the synthetic carbon quantum dots have a relatively-high fluorescent quantum yield; meanwhile, the carbon quantum dots solution have better selectivity to HRP protein. However, the better selectivity is only to horseradish peroxidase, and its low fluorescence intensity limits its application range.

At present, there is no method for preparing quantum dots which simultaneously satisfy large fluorescence intensity, high fluorescence quantum yield, simple preparation method, mass production, low production cost and wide application range.

SUMMARY

In order to solve the problems of small fluorescence intensity, low yield, complicated preparation method, and limited application range, the present invention provides a method for preparing biomass-based high-efficiency fluorescent graphene quantum dots.

A Method for preparing biomass-based high-efficiency fluorescent graphene quantum dots, includes hydrothermal reaction of composite carbon source, nitrogen source, polyvalent metal ion and water.

Preferably, the composite carbon source is citric acid and biomass-based extract.

Preferably, the biomass-based extract is one of the chlorophyll crude extracts of the fresh leaves of Bauhinia, the fresh leaves of *Lagerstroemia speciosa*, the fresh leaves of *Pinus massoniana*, the fresh leaves of citrus and the flower of *Lagerstroemia speciosa*.

Preferably, the biomass-based extract is the chlorophyll crude extract from fresh leaves of Bauhinia.

Preferably, the multivalent metal ion is one of $Mg^{2+}$, $Cu^{2+}$, $Zn^{2+}$, $Au^{3+}$ and $Fe^{3+}$.

Preferably, the nitrogen source is ethylenediamine.

Preferably, by weight, including 3-10 parts of citric acid, 5-6 parts of biomass-based extract, 0.4-3 parts of nitrogen source, 0.04-0.20 parts of polyvalent metal ions, and 70-140 parts of water.

Preferably, the composite carbon source is prepared by cutting leaves or flowers, adding a mixture of petroleum ether and ethanol to obtain an extract, and washing the extract with a saturated NaCl solution, and the obtained organic phase is washed with water, dried, and concentrated by evaporation. Biomass-based extract, then mixed with citric acid to obtain the composite carbon source.

Preferably, the leaves or flowers are one of fresh leaves of Bauhinia, fresh leaves of *Lagerstroemia speciosa*, fresh leaves of *Pinus massoniana*, fresh leaves of citrus, and flowers of *Lagerstroemia speciosa*.

Preferably, petroleum ether:ethanol=2:1 by volume.

Preferably, by weight, leaves or flowers: the mixture of petroleum ether and ethanol=1:4-6.

Preferably, by weight, leaves or flowers: the mixture of petroleum ether and ethanol=1:5.

Preferably, the obtained organic phase are washed with water and dried over anhydrous sodium sulfate.

Preferably, the preparation method of biomass-based high-efficiency fluorescent graphene quantum dots includes the following steps:

(1) Mixing the composite carbon source and the nitrogen source, and then adding water, stirring and dissolving to obtain a mixture A;

(2) Adding polyvalent metal ions to the mixture A, heating and reacting to obtain a crude product;

(3) The crude product purified by dialysis to obtain a purified product.

Preferably, in the step (1), the stirring speed is 120-600 rpm, and the stirring time is 5-10 min.

Preferably, in the step (2), the stirring speed is 120-600 rpm and the stirring time is 5-10 min.

Preferably, in the step (2), the temperature is raised to 170-190° C., and the reaction is 120-300 min.

Preferably, in the step (3), the dialysis process is to purify the product by loading the crude product into a dialysis bag and purifying it with pure water as dialysate.

Preferably, in the step (3), the dialysis process is carried out by charging the crude product into a 1000 Da dialysis bag, using purified water as dialysate, and changing purified water every 5 hours to obtain the purified product after 3 days of dialysis.

Preferably, the preparation method of biomass-based high-efficiency fluorescent graphene quantum dots includes the following steps:

(1) The composite carbon source (3-10 parts of citric acid, 5-6 parts of biomass-based extract), 0.4-3 parts of nitrogen source, and 70-140 parts of water are stirred and dissolved to obtain a mixture A.;

where in, the composite carbon source is prepared by cutting 1 part of leaves or flowers, adding 4-6 parts of petroleum and ethanol mixture with volume ratio of 2:1 to obtain an extract, and washing the extract with a saturated NaCl solution. The obtained organic phase is washed twice with water, dried over anhydrous sodium sulfate, and concentrated by evaporation to obtain a biomass-based extract, which is then mixed with citric acid to obtain a composite carbon source.

(2) Adding 0.04-0.20 parts of polyvalent metal ions to the mixture A to obtain a specific complex as a template, stirring and heating the specific complex to 170-190° C., and reacting for 120-300 min to obtain a crude product;

(3) Putting the crude product into a 1000 Da dialysis bag, using purified water as the dialysate, changing the purified water every 5 hours, then the purified product can be obtain after dialysis for 3 days.

The invention also provides the biomass-based high-efficiency fluorescent graphene quantum dots prepared by the above preparation method.

The "biomass" in the present invention refers to a crude chlorophyll extract which is prepared by a classical chlorophyll extraction method using leaves or flowers of a specific tree as a raw material, and mainly contains chlorophyll (such as chlorophyll a, chlorophyll b, etc.)

The "graphene quantum dot" in the present invention refers to a nanosheet composed of an oligo (3-6 layers) of graphene and having a two-dimensional size of less than 10 nm and having high-efficiency fluorescence characteristics.

Principle: Based on the main component of chlorophyll, porphyrin and polyvalent metal ions can form a complex by coordination, and the complex is used as a template to control nucleation, which affects the morphology of carbon quantum dots formed during hydrothermal reaction.

Chlorophyll extract (biomass) from different sources, wherein the porphyrin parent ring has the same structure, but there are some differences in the substituents, resulting in a significant difference in the fluorescence intensity of the synthesized product. In the present invention, $Mg^{2+}$, $Cu^{2+}$, $Zn^{2+}$, $Au^{3+}$, $Fe^{3+}$ plasma makes the prepared quantum dots have the best fluorescence characteristics.

Ethylenediamine is a nitrogen source which can also act as a small molecular ligand for complexing with polyvalent metal ions.

The product of the invention is a graphene type carbon quantum dot, referred to as a graphene quantum dot, which is different from ordinary carbon quantum dots. The former is characterized by flaky nanoparticles, the latter is spherical nanoparticles.

Compared with the current technology, the beneficial effects of the present invention are:

1. A high-efficiency fluorescent nitrogen-doped carbon quantum dots (N-CQDs) can be synthesized in one step by using biomass (green chlorophyll extract) derived from fresh leaf extract of purple flower and citric acid as a composite carbon source;

2. It is easier to prepare "oligo-layer" graphene type carbon quantum dots (N-GQDs) in one step by adding polyvalent metal ions to the synthesis system ($Mg^{2+}$, $Cu^{2+}$, $Zn^{2+}$, $Au^{3+}$, $Fe^{3+}$) to form complexes as the template;

3. The graphene-type carbon quantum dots prepared by the invention have higher fluorescence intensity than ordinary carbon quantum dots.

DESCRIPTION OF THE EMBODIMENTS

The invention will be further described in conjunction with the specific embodiments thereof, and the advantages and features of the present invention will be more apparent from the description. It should be understood that the details and forms of the technical solutions of the present invention may be modified or replaced without departing from the spirit and scope of the present invention, but such modifications and substitutions fall within the scope of the present invention.

Example 1

Chlorophyll extraction method: 2 g of chopped fresh Bauhinia leaves were placed in a mortar, and 10 mL of a mixture of petroleum ether and ethanol ($V_{petroleum\ ether}/V_{ethanol}=2:1$) was added for grinding. The extract was transferred to a separatory funnel with a dropper, 5 mL of saturated NaCl solution was added to remove the water-soluble substance, the aqueous layer was separated, and the organic phase was washed twice with 5 mL of distilled water. The organic layer was transferred to a dry small conical flask and dried over anhydrous sodium sulfate. After drying, it was filtered into a round bottom flask and concentrated to 1 mL by evaporation on a water bath.

Figure 1:
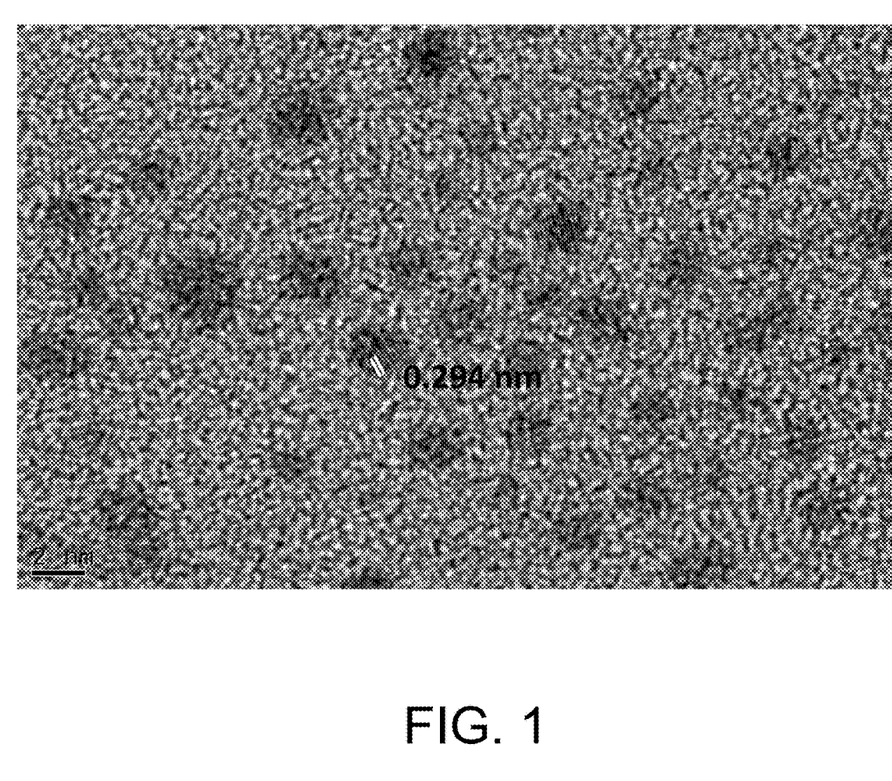
FIG. 1 TEM of nitrogen-doped graphene quantum dots (N-GQDs) of Example 1.
Figure 2:
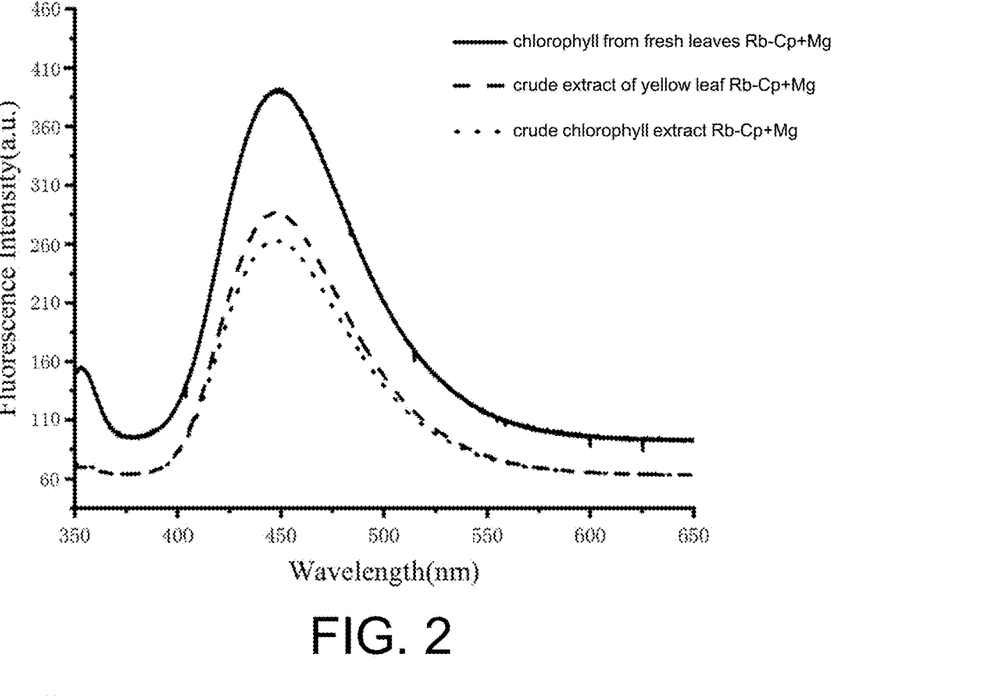
FIG. 2 Fluorescence spectra of nitrogen-doped graphene quantum dots (N-GQDs) of Example 1.

5 g of citric acid, 10 g of chlorophyll from fresh leaves of Bauhinia, 2.403 g of ethylenediamine was added to a beaker containing 120 ml of pure water, stirred and dissolved, then 0.184 g of magnesium chloride was added, stirred and dissolved, and the solution was divided into 6 polytetrafluoroethylene inner liners, 20 ml of each inner liner, the inner liner was placed in a stainless steel reaction vessel, and reacted at 180° C. for 150 min to obtain a crude product. The crude product was placed into a 1000 Da dialysis bag, and pure water was used as the dialysate, the water was changed every 5 hours, and purified product was obtained after dialysis for 3 days. After purification of the crude product, 350 μL purified product was diluted 1 million times, and then the fluorescence spectrum was tested (as shown in FIG. 2), the TEM test results of the corresponding samples (as shown in FIG. 1) showed that the carbon quantum dots had an average diameter of less than 5 nm and distinct characteristics of nitrogen-doped graphene quantum dots. The distinct characteristics of nitrogen-doped graphene quantum dots (N-GQDs): lattice fringes, and the lattice fringe width of such N-doped nitrogen-doped graphene quantum dots (N-GQDs) is 0.294 nm.

The invention were also carried out a controlled variable test on the crude chlorophyll extract and the crude extract of the yellow leaf of the yellow flower of Bauhinia, and only changing the leaves of the bauhinia, the other conditions and steps were unchanged. The fluorescence intensity spectrum test was as shown in FIG. 2. It can be seen from FIG. 2 that the chlorophyll from fresh leaves was beneficial to enhance the fluorescence intensity of nitrogen-doped graphene quantum dots, and the fluorescence quantum yield was higher than 65% (Quinol sulfate is the reference standard).

Example 2

Chlorophyll extraction method: same as in the example 1.

Figure 3:
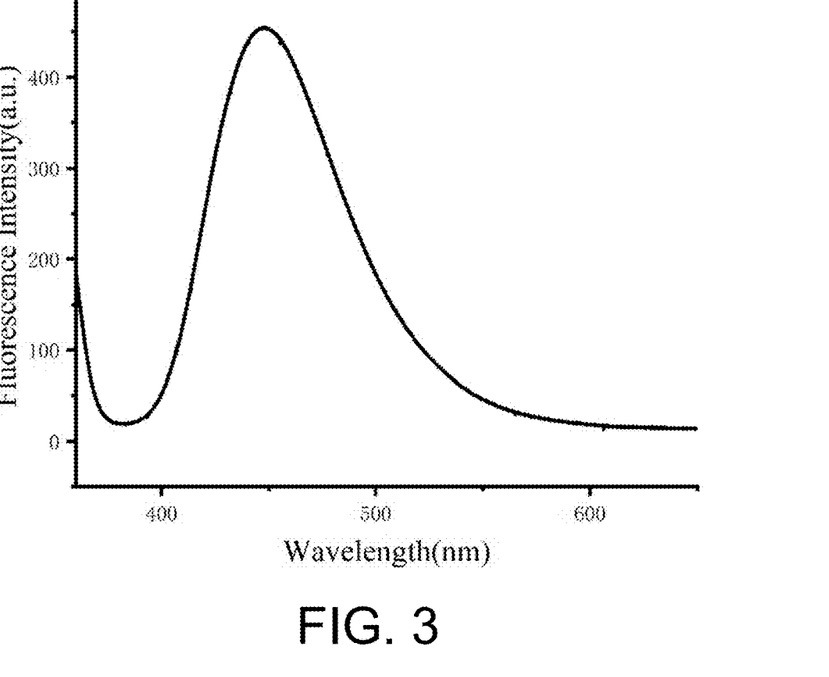
FIG. 3 Fluorescence spectra of nitrogen-doped graphene quantum dots (N-GQDs) of Example 2.

8 g of citric acid, 10 g of chlorophyll from fresh leaves of Bauhinia, 2.403 g of ethylenediamine was added to a beaker containing 120 ml of pure water, stirred and dissolved, then 0.1 g of magnesium chloride was added, stirred and dissolved, and the solution was divided into 6 polytetrafluoroethylene inner liners, 20 ml of each inner liner, the inner liner was placed in a stainless steel reaction vessel, and reacted at 180° C. for 150 min to obtain a crude product. The crude product was placed into a 1000 Da dialysis bag, and pure water was used as the dialysate, the water was changed every 5 hours, and purified product was obtained after dialysis for 3 days. After purification of the crude product, 350 μL purified product was diluted 1 million times, and then the fluorescence spectrum was tested (as shown in FIG. 3).

Example 3

Chlorophyll extraction method: same as in the example 1.

Figure 4:
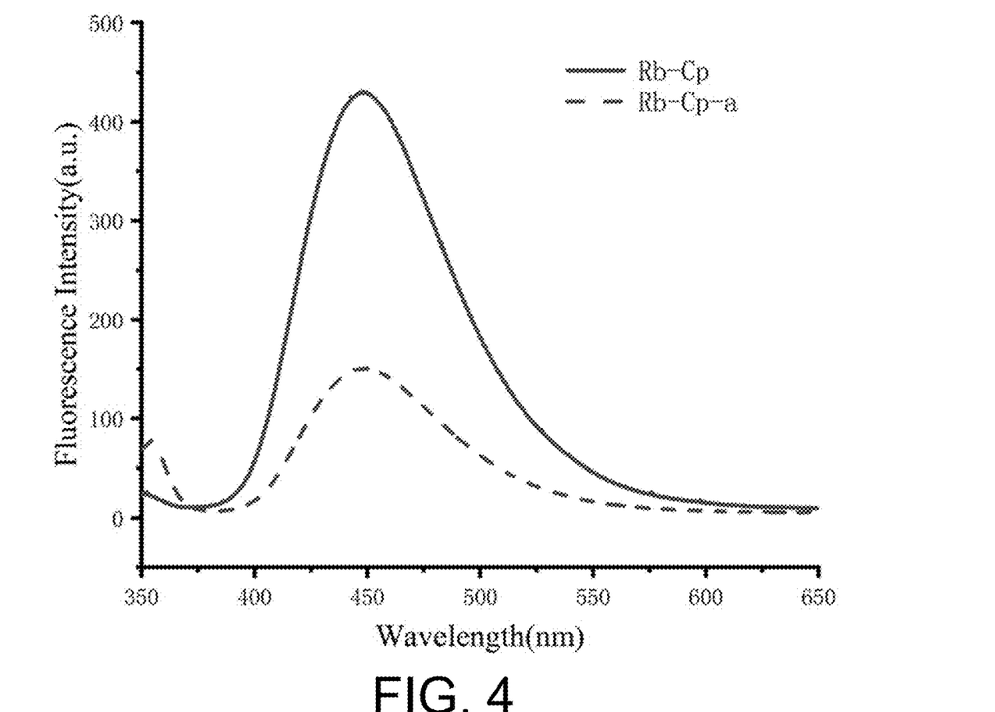
FIG. 4 Fluorescence spectra of nitrogen-doped graphene quantum dots (N-GQDs) of Example 3 and Comparative Example 2; Rb-Cp is the fluorescence spectrum curve of Example 3, Rb-Cp-a is the fluorescence spectrum curve of Comparative Example 2.

5 g of citric acid, 10 g of chlorophyll from fresh leaves of Bauhinia, 2.403 g of ethylenediamine was added to a beaker containing 120 ml of pure water, stirred and dissolved, then 0.07 g of gold chlorate was added, stirred and dissolved, and the solution was divided into 6 polytetrafluoroethylene inner liners, 20 ml of each inner liner, the inner liner was placed in a stainless steel reaction vessel, and reacted at 180° C. for 150 min to obtain a crude product. The crude product was placed into a 1000 Da dialysis bag, and pure water was used as the dialysate, the water was changed every 5 hours, and purified product was obtained after dialysis for 3 days. After purification of the crude product, 350 μL purified product was diluted one million times, and then the fluorescence spectrum was tested (as shown in FIG. 4).

Example 4

Chlorophyll extraction method: 2 g of freshly chopped leaves of *Lagerstroemia speciosa* were placed into a mortar, and 8 mL of petroleum ether and ethanol mixture was added for grinding ($V_{petroleum\ ether}/V_{ethanol}=2:1$). The extract was transferred to a separatory funnel with a dropper, 5 mL of saturated NaCl solution was added to remove the water-soluble substance, the aqueous layer was separated, and the organic phase was washed twice with 8 mL of distilled water. The organic layer was transferred to a dry small conical flask and dried over anhydrous sodium sulfate. After drying, it was filtered into a round bottom flask and concentrated to 1 mL by evaporation on a water bath.

3 g citric acid, 6 g of fresh chlorophyll extract from fresh leaves of *Lagerstroemia speciosa*, 0.4 g of ethylenediamine was added to a beaker containing 140 ml of pure water, stirred and dissolved, then 0.04 g of copper chloride was added, stirred and dissolved, and the solution was dispensed into 7 inner liners, 20 ml of each inner liner, the inner liner was placed in a stainless steel reaction kettle, and reacted at 170° C. for 120 min to obtain a crude product. The crude product was placed in a 1000 Da dialysis bag, pure water was used as the dialysate, the water was changed every 6 hours, and purified product was obtained after dialysis for 3 days.

Example 5

Chlorophyll extraction method: 2 g of freshly chopped leaves of *Pinus massoniana* were placed into the mortar, and 12 mL of petroleum ether and ethanol mixture was added for grinding ($V_{petroleum\ ether}/V_{ethanol}$=2:1). The extract was transferred to a separatory funnel with a dropper, 6 mL of saturated NaCl solution was added to remove the water-soluble substance, the aqueous layer was separated, and the organic phase was washed twice with 10 mL of distilled water. The organic layer was transferred to a dry small conical flask and dried over anhydrous sodium sulfate. After drying, it was filtered into a round bottom flask and concentrated to 1 mL by evaporation on a water bath.

10 g citric acid, 5 g of fresh chlorophyll extract from fresh leaves of *Pinus massoniana*, 3 g of ethylenediamine was added to a beaker containing 100 ml of pure water, stirred and dissolved, then 0.2 g of zinc chloride was added, stirred and dissolved, and the solution was dispensed into 5 inner liners, 20 ml of each inner liner, the inner liner was placed in a stainless steel reaction kettle, and reacted at 190° C. for 300 min to obtain a crude product. The crude product was placed in a 1000 Da dialysis bag, pure water was used as the dialysate, the water was changed every 5 hours, and purified product was obtained after dialysis for 4 days.

Example 6

Chlorophyll extraction method: 2 g of freshly chopped flower of the crape myrtle were placed into the mortar, and 8 mL of petroleum ether and ethanol mixture was added for grinding ($V_{petroleum\ ether}/V_{ethanol}$=2:1). The extract was transferred to a separatory funnel with a dropper, add 5 mL of saturated NaCl solution was added to remove the water-soluble substance, the aqueous layer was separated, and the organic phase was washed twice with 8 mL of distilled water. The organic layer was transferred to a dry small conical flask and dried over anhydrous sodium sulfate. After drying, it was filtered into a round bottom flask and concentrated to 1 mL by evaporation on a water bath.

8 g citric acid, 5.5 g of fresh chlorophyll extract from fresh flower of the crape myrtle, 1.5 g of ethylenediamine was added to a beaker containing 120 ml of pure water, stirred and dissolved, then 0.1 g of ferric chloride was added, stirred and dissolved, and the solution was dispensed into 6 inner liners, 20 ml of each inner liner, the inner liner was placed in a stainless steel reaction kettle, and reacted at 180° C. for 200 min to obtain a crude product. The crude product was placed in a 1000 Da dialysis bag, pure water was used as the dialysate, the water was changed every 3 hours, and purified product was obtained after dialysis for 4 days.

Comparative Example 1

Compared to Example 1, magnesium chloride was not included.

Figure 5:
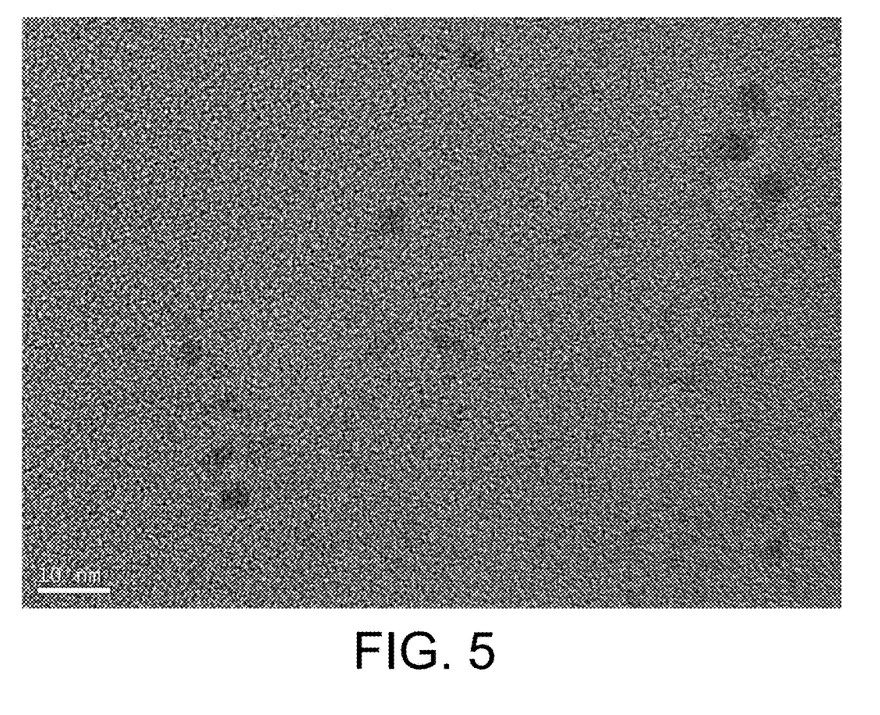
FIG. 5 TEM of nitrogen-doped carbon quantum dots (N-CQDs) of Comparative Example 1.

5 g of citric acid, 10 g of chlorophyll from fresh leaves of Bauhinia, 2.403 g of ethylenediamine was added to a beaker containing 120 ml of pure water, stirred and dissolved. The solution was divided into 6 polytetrafluoroethylene inner liners, 20 ml of each inner liner, the inner liner was placed in a stainless steel reaction vessel, and reacted at 180° C. for 150 min to obtain a crude product. The crude product was placed into a 1000 Da dialysis bag, and pure water was used as the dialysate, the water was changed every 5 hours, and purified product was obtained after dialysis for 3 days. The TEM test results of the corresponding samples were shown in FIG. 5.

Comparative Example 2

Compared with Example 3, 95% by weight of chlorophyll A was used instead of chlorophyll of fresh leaves of Bauhinia.

Figure 6:
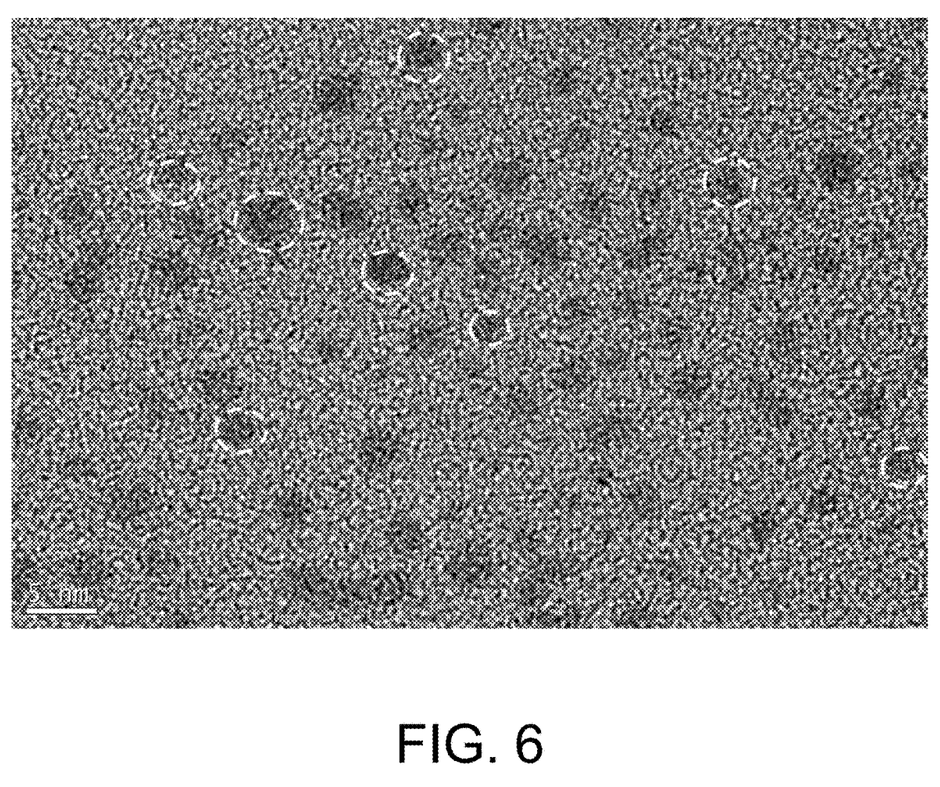
FIG. 6 TEM of nitrogen-doped graphene quantum dots (N-GQDs) of Comparative Example 2.

5 g of citric acid, 10 g of chlorophyll A (95 wt %), 2.403 g of ethylenediamine was added to a beaker containing 120 ml of pure water, stirred and dissolved, then 0.07 g of gold chlorate was added, stirred and dissolved, and the solution was divided into 6 polytetrafluoroethylene inner liners, 20 ml of each inner liner, the inner liner was placed in a stainless steel reaction vessel, and reacted at 180° C. for 150 min to obtain a crude product. The crude product was placed into a 1000 Da dialysis bag, and pure water was used as the dialysate, the water was changed every 5 hours, and obtain purified product after dialysis for 3 days. After the crude product was properly purified, 350 μL purified product was diluted 1 million times, and then the fluorescence spectrum was tested (as shown in FIG. 4). The TEM test results of the corresponding samples (as shown in FIG. 6) show that the carbon quantum dots have an average diameter of less than 5 nm and have distinct characteristics (lattice stripes) characteristic of nitrogen-doped graphene quantum dots (N-GQDs).

Comparative Example 3

Compared with Example 1, the chlorophyll of the fresh leaves of cypress was replaced by the chlorophyll of the fresh leaves of cypress, and the other conditions were unchanged.

Comparative Example 4

Compared with Example 1, the chlorophyll extraction method was different, and other conditions were unchanged.

Chlorophyll extraction method: 2 g of freshly chopped leaves were putted into a mortar, 15 mL of ethanol were added, and grinded properly. the extract was transferred to a separatory funnel with a dropper and wash twice with 5 mL of distilled water. The organic layer was transferred to a dry small conical flask and dried over anhydrous sodium sulfate, then filtered into a round bottom flask and concentrated to 1 mL by evaporation on a water bath.

Test Example 1

For the products of Examples 1-6 and Comparative Examples 1-4, the fluorescence intensity test was performed. The experimental method was: after the crude product was properly purified, 350 μL purified product was diluted one million times to make the test peak in the range of 100-1000, and then the fluorescence spectrum were test using excitation light with a wavelength of 365 nm.

The experimental results are as follows:

| group | The fluorescence intensity(a.u.) |
|---|---|
| Example 1 | 407 |
| Example 2 | 453 |
| Example 3 | 436 |
| Example 4 | 409 |
| Example 5 | 422 |
| Example 6 | 417 |
| Comparative Example 1 | 105 |
| Comparative Example 2 | 152 |
| Comparative Example 3 | 163 |
| Comparative Example 4 | 201 |

Test Example 2

Drying at 105° C. for 10 h, drying the "composite carbon source", in which the total amount of solid matter was recorded as value a. After the hydrothermal reaction product was properly purified, it was dried at 105° C. for 10 h, corresponding to solid The total amount of the contents was recorded as the value b; Yield=b/a*100%.

The experimental results are as follows:

| group | Yield(%) |
|---|---|
| Example 1 | 85.1 |
| Example 2 | 86.9 |
| Example 3 | 85.8 |
| Example 4 | 95.3 |
| Example 5 | 82.4 |
| Example 6 | 89.4 |
| Comparative Example 2 | 80.2 |
| Comparative Example 3 | 72.9 |
| Comparative Example 4 | 76.4 |

The comprehensive test results showed that the application has the following advantages:

1. A high-efficiency fluorescent nitrogen-doped carbon quantum dots (N-CQDs) can be synthesized in one step by using biomass (green chlorophyll extract) derived from fresh leaf extracts of purple flower and citric acid as composite carbon source;

2. It is easier to prepare "oligo-layer" graphene type carbon quantum dots (N-GQDs) in one step by adding polyvalent metal ions to the synthesis system ($Mg^{2+}$, $Cu^{2+}$, $Zn^{2+}$, $Au^{3+}$, $Fe^{3+}$);

3. The graphene-type carbon quantum dots prepared by the invention have higher fluorescence intensity than ordinary carbon quantum dots, and its fluorescence quantum yield is higher than 65% (with quinoline sulfate as a reference standard).

The technical means disclosed in the solution of the present invention is not limited to the above-disclosed technical means, and includes a technical solution composed of any combination of the above technical features. The above is a specific embodiment of the present invention, and it should be noted that those skilled in the art can also make several improvements and modifications without departing from the principles of the present invention, which will also be regarded as the scope of protection of the present invention.

What is claimed is:

1. A method for preparing biomass-based high-efficiency fluorescent graphene quantum dots, wherein the biomass-based high-efficiency fluorescent graphene quantum dots are prepared from composite carbon source, nitrogen source, polyvalent metal ion and water; comprising the following steps:
    (1) Mixing the composite carbon source and the nitrogen source, and then adding water, stirring and dissolving to obtain a mixture A;
    (2) Adding the polyvalent metal ions to the mixture A, and after stirring, heating and reacting to obtain a crude product;
    (3) The crude product is purified by dialysis to obtain a purified product.

2. The method according to claim 1, wherein the composite carbon source is citric acid and biomass-based extract, and the nitrogen source is ethylenediamine.

3. The method according to claim 2, wherein the biomass-based extract is selected from one or more of the following: crude chlorophyll extracts of fresh leaves of Bauhinia, crude chlorophyll extracts of fresh leaves of *Lagerstroemia speciosa*, crude chlorophyll extracts of fresh leaves of *Pinus massoniana*, crude chlorophyll extracts of fresh citrus leaves of *Lagerstroemia speciosa* and crude chlorophyll extracts of flowers of *Lagerstroemia speciosa*.

4. The method according to claim 1, wherein the polyvalent metal ion is one of $Mg^{2+}$, $Cu^{2+}$, $Zn^{2+}$, $Au^{3+}$ and $Fe^{3+}$.

5. The method according to claim 2, wherein the citric acid is present in an amount of 3-10 parts by weight, the biomass-based extract is present in an amount of 5-6 parts by weight, the nitrogen source is present in an amount of 0.4-3 parts by weight, the polyvalent metal ions are present in an amount of 0.04-0.20 parts by weight, and the water is present in an amount of 70-140 parts by weight.

6. The method according to claim 1, wherein in the step (1), the stirring speed is 120-600 rpm, and the stirring time is 5-10 min.

7. The method according to claim 1, wherein in the step (2), the stirring speed is 120-600 rpm, the stirring time is 5-10 min, and after stirring, the temperature is raised to 170-190° C., and the reacting time is 120-300 min.

8. The method according to claim 1, wherein in the step (3), the dialysis process is carried out by charging the crude product into a 1000 Da dialysis bag, using purified water as dialysate, and changing purified water every 3-6 hours to obtain the purified product after 3 days of dialysis.

* * * * *